US006174731B1

(12) United States Patent
Strochkova et al.

(10) Patent No.: US 6,174,731 B1
(45) Date of Patent: Jan. 16, 2001

(54) REAGENT FOR THE PH-METRIC DETERMINATION OF LOW ACID NUMBERS IN PETROLEUM OILS

(75) Inventors: Elena M. Strochkova; Yakov I. Tur'yan; Oleg Y. Berezin; Ilya Kuselman; Shenhar Avinoam, all of Jerusalem (IL)

(73) Assignee: State of Israel, The Ministry of Industry and Trade, The National Physical Laboratory, Jerusalem (IL)

( * ) Notice: Under 35 U.S.C. 154(b), the term of this patent shall be extended for 0 days.

(21) Appl. No.: 09/104,154

(22) Filed: Jun. 24, 1998

(51) Int. Cl.$^7$ ..................................................... G01N 31/16
(52) U.S. Cl. ............................ 436/163; 436/17; 436/100; 73/53.05; 252/408.1
(58) Field of Search ................. 436/17, 100, 163; 252/408.1; 422/75, 76; 73/19.11, 53.05, 61.41, 53.01

(56) References Cited

U.S. PATENT DOCUMENTS

| | | | |
|---|---|---|---|
| 2,953,439 | * | 9/1960 | Elliott et al. ..................... 422/57 X |
| 3,580,704 | * | 5/1971 | Pickup et al. ..................... 422/56 X |
| 4,098,575 | * | 7/1978 | Matsushita ........................ 422/56 X |
| 4,654,309 | * | 3/1987 | Mlinar et al. .................... 422/56 X |

FOREIGN PATENT DOCUMENTS

| | | |
|---|---|---|
| 0151278B1 | 8/1985 | (EP) . |
| 110192 | 10/1994 | (IL) . |
| 989476 | 1/1983 | (SU) . |

OTHER PUBLICATIONS

Chem Abstract 121:118767a (1994).
Ya. I. Tur'yan, V. F. Pokhodzei and D.A. Krukier, Izv. Vyssh. Uchebn. Zaved.,Pisshch Technol. , Krasnodar, USSR, No. 3, 1989, pp. 39–41.
O. Yu. Berezin, Ya I. Tur'yan, I. Kuselman and A. Shenhar, Talanta, 42, 1995, pp. 507–517.

\* cited by examiner

*Primary Examiner*—Terrence R. Till
*Assistant Examiner*—Theresa T. Snider
(74) *Attorney, Agent, or Firm*—Edwin D. Schlinder

(57) ABSTRACT

A reagent for pH-metric acid number determination in a petroleum oil with low acid numbers (AN≦0.03 mg KOH/g oil) includes a salt of a strong base and a weak acid, and, an alkali in a mixture of water and an alcohol. The salt of a strong base and a weak is, preferably, sodium benzoate in a concentration of 0.02 to 0.1 M. The alcohol is, preferably, isopropanol in a concentration of from 50% to 80% by volume. The alkali is, preferably, an hydroxide and, most preferably, potassium hydroxide. The alkali should be adjusted to provide a pH'o, which is the pH of an equivalence-point on a titration curve of a strong acid added to a test portion of sodium benzoate, water and isopropanol.

24 Claims, 1 Drawing Sheet

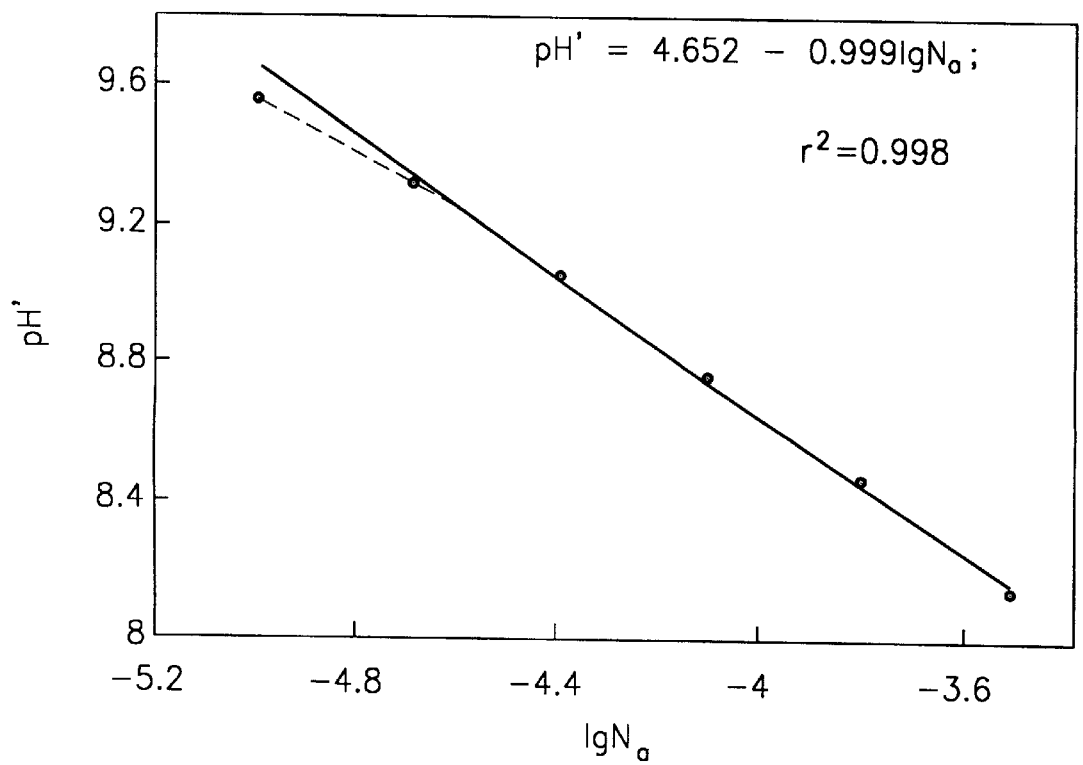
FIGURE

REAGENT FOR THE PH-METRIC DETERMINATION OF LOW ACID NUMBERS IN PETROLEUM OILS

FIELD OF THE INVENTION

The invention is intended for pH-metric determination of low acid numbers (AN) in petroleum oils such as Transformer, White or Basic and other oils for which $AN \leq 0.03$ mg KOH/g oil (Specification for Unused Mineral Insulating Oils for Transformers and Switchgear, IEC Standard, Geneva, Switzerland, 1982).

BACKGROUND OF THE INVENTION

Standards for AN determination in petroleum oils are based on the acid-base titration techniques in non-aqueous systems (American National Standards D3339-87; International Electrotechnical Commission Standard, 296, 1982). These techniques are time and labour consuming, and difficult for automation. There are used toxic and flammable solvents, for example toluene, as well as non-aqueous alkali titrants which are very sensitive to carbon dioxide contamination from the atmosphere. Difficulties are increasing at the determination of $AN \leq 0.03$ mg KOH/g oil (Transformer, White, Basic and other oils). In this case the titration should be carried out in a nitrogen atmosphere and besides the indicator, the colour witness (cobalt nitrate solution) is used also for more correct determination of the end point of the titration (American National Standard D3339-87; International Electrotechnical Commission Standard 296, 1982).

The pH-metric technique developed earlier by us for determination of acid value in vegetable oils and corresponding reagent-precursor (0.20 M triethanolamine in a mixture 1+1 of water and isopropanol, (vol.); Ya. I. Tur'yan, O. Berezin, I. Kuselman and A. Shenhar, Israeli Pat. Appl. 110192, 01.07.94) are free from indicated drawbacks. However, its limit of quantitation is 0.03 mg KOH/g oil. It is sufficient for vegetable oils but it does not satisfy requirements of the petroleum oil analysis.

Another reagent (0.01 M NaOAc in water: Ya. I. Tur'yan, V. F. Pokhodzei and D. A. Krukier, Izv. Vyssh. Uchebn. Zaved., Pisshch. Technol., Krasnodar, USSR, No. 3, 1989, p. 39) was developed for pH-metric acid value determination in aqueous samples. This reagent allowed to decrease the limit of quantitation, but is not suitable for AN determination in oils since acid from oils cannot be extracted completely into an aqueous reagent. The aim of the present invention is to provide a reagent for the pH-metric AN determination in petroleum oils in the range $AN \leq 0.03$ mg KOH/g oil.

BRIEF DESCRIPTION OF THE DRAWING FIGURE

The single FIGURE is a graphical display of the dependence of pH1 vs. IgNa.

The Novel Reagent

The impossibility to use as a reagent-precursor for AN determination in oils at $AN \leq 0.03$ KOH/g oil is due to the relatively high basicity of the amine in the reagent and corresponding influence of the amine hydrolysis (solvolysis) products on the results of the low level AN determination. A decrease of the amine concentration does not solve this problem and it is necessary to decrease the basicity. For this purpose according to the invention there is used as a weak base an anion of a weak acid being part in a salt of a strong base and weak acid. The solvent was the same as that developed for the reagent-precursor: a mixture of an alcohol and water.

The salt should be in large excess to the total concentration $N_a$ of acids in the mixture "reagent-oil" for ensuring linearity of the dependence pH vs $IgN_a$ (O. Yu. Berezin, Ya. I. Tur'yan, I. Kuselman and A. Shenhar, Talanta, 42, 1995, p. 507). A high excess of the salt stabilizes also the ionic strength of the reagent. So, a special addition of an indifferent salt to the reagent for this purpose, as it was done for the reagent-precursor, in our case was unnecessary.

A variety of salts of strong bases and weak acids may be used. One of choice is sodium benzoate (NaBen) in the range of concentrations between about 0.02 to about 0.1 M. The choice of the alcohol and its concentration depends on the weak base and analyzed oils. Isopropanol was chosen in a range of concentration in a mixture isopropanol/water was 50 to 80% (by vol.). Concentrations of isopropanol below 80% ensures practical insolubility of petroleum oils in the solvent, and hence the influence of an oil on the solvent properties is absent. An oil sample and the proposed reagent form a two-phase system (emulsion). Increase of the water concentration in the solvent>50% leads to incomplete extraction of the acids. On the other hand, for stable work of the pH-metric sensor the reagent must contain a maximum of water in the solvent. Therefore optimal composition of the solvent is water and isopropanol, 1+1, by vol.

The completeness of the acid extraction by the reagent depends also of the concentration of NaBen and at its value 0.05 M allows to use the ratio of the mass (g) of an oil sample to the volume (mL) of the reagent up to 1.1:1.0. The extraction of acids from an oil sample into the reagent is carried out during 2–3 min of stirring.

Since the pH measurements in non-aqueous media are carried out with electrodes calibrated by aqueous buffer solutions, obtained pH values are conditional ones ($pH^1$).

The conditional pH of the novel reagent ($pH_o'$) was determined by the pH-metric titration of a strong acid (for example, HCl) specifically added to the test portion of Naben in the solvent. Note, the $pH_o'$ value depends on the electrodes used for pH measurements and can vary approximately in the range 9.4–10.4. Obtained by us $pH_o'=9.87\pm0.02$ is lower than for the reagent-precursor ($pH_o'=11.30$). Therefore the novel reagent is less sensitive to carbon dioxide contamination from the atmosphere than its precursor. For adjustment of the $pH_o'$ of the reagent under preparation, a small volume of aqueous KOH solution is added.

Thus, optimal composition of the reagent is the following: 0.05 M NaBen in a solvent consisting of water and isopropanol, 1+1, (vol.) and KOH added up to $pH_o'$.

The important analytical characteristic of the reagent is the dependence of pH' vs Ig $N_a$. According to the theory (O. Yu. Berezin, Ya. I. Tur'yan, I. Kuselman and A. Shenhar, Talanta, 42, 1995, p. 507) this dependence should be linear with the slope equal to 1. The experimental dependence pH' vs Ig $N_a$ in FIGURE corresponds to this requirement: the squared correlation coefficient is 0.998, the slope is 0.999. An analogous dependence is observed in the presence of an oil sample added to the reagent, i.e. in the "reagent-oil" two-phase system (emulsion). Thus, it is important to emphasize that neither the nature of the studied oils nor the quantity of an oil sample, has any influence on the character of the pH' vs Ig $N_a$ dependence (FIGURE) at the ratio of the sample mass (g) to the reagent volume (mL) up to 1.1:1.0.

The linear range of the dependence pH' vs Ig $N_a$ obtained by us was observed for $N_a$ from $2.0 \cdot 10^{-5}$ M to $3.1 \cdot 10^{-4}$ M. At $N_a < 2.0 \cdot 10^{-5}$ M a deviation of the dependence from the linear form takes place (FIG). It can be explained by the influence of hydrolysis (solvolysis) of Ben-anion. From the low limit of $N_a$ in the linear range of the dependence ($2.0–10^{-5}$ M) follows that the limit of determination (LOD) for AN is $AN_{LOD}=1.0–10^{-3}$ mg KOH/g oil at the maximum mass of an oil sample 55 g and a reagent volume of 50 mL. This value of the limit of the determination is ~30 times smaller than that for the reagent-precursor and it is sufficient for the characterization of the Transformer, White, Basic and others oils with a low AN.

Since the standard addition method is used for AN determination (see below), maximum $N_a$ under determination should be 2–3 times lower than the upper limit of $N_a$ in the linear range of the dependence pH' vs $IgN_a$ ($3.1–10^{-4}$ M), i.e. be $1.0–10^{-4}–1.5–10^{-4}$ M. One can see that the concentration of the salt $C_{NaBen}=0.05$ M and corresponding concentration of the weak base (Ben$^-$) are sufficiently large in relation to these $N_a$ values.

The Use of the Novel Reagent

The AN can be determined in accordance to the standard addition method by the introduction of a standard acid into the "reagent-oil" mixture (Ya. I. Tur'yan, O. Yu. Berezin, I. Kuselman and A. Shenhar. Am. Oil. Chem. 73, 1996p. 295) and calculation by the following formula:

$$AN=56.11 \cdot N_{st} \cdot V_{st}/[m \cdot (10^{\Delta pH}-1)] \text{ mg KOH/g oil}, \quad (1)$$

where $N_{st}$ is the standard acid concentration, M; $V_{st}$ is the standard addition volume, mL, which is considerably lower than the volume of the reagent (50 mL); $\Delta pH=pH'_1-pH'_2$; $pH'_1$ is pH of the mixture "oil-reagent"; $pH'_2$ is pH after addition of the standard acid to the previous mixture.

An aqueous HCl solution (0.03–0.04 M) as a standard acid can be used: $V_{st}=0.05–0.1$ mL. Suitable mass of the oil sample m=10–55 g.

EXAMPLES

AN values were determined in commercial petroleum oils such as Transformer, White, Basic oils and in a model of White oil fortified by naphtenic acid. The AN values in the oil samples were first determined by the standard titration method (American National Standard D 3339-87). In accordance with this standard a weighed oil sample was added to a solvent consisting of toluene, isopropyl alcohol and water. The solution was titrated at room temperature under nitrogen atmosphere against standardized 0.01 M potassium hydroxide in isopropyl alcohol to the stable end-point of the added p-naphtholbenzein indicator. For titration 2 mL microburette was used with 0.01 mL divisions and a drop size of 0.008 mL. The average $AN_s$ values were obtained for 5 titrations-replicates. The replicate standard deviations $S_s$ were calculated from the same data (Table). The results were accepted as correct.

The same oil samples were taken for AN determination by the novel reagent and novel pH-metric technique (Examples 1–5). Composition of the reagent was 0.05 M NaBen in a solvent including water and isopropyl alcohol, 1+1, vol. $pH'_0=9.87\pm0.02$. pH-Meter PHM 95, glass electrode G 202 C and Ag/AgCl, KCl 3 M electrode REF 251 from Radiometer, Denmark, were used. The precision of pH measurements was ±0.01. The average $AN_p$ values were obtained, each for 5 pH-metric replicates, with corresponding replicate standard deviations $S_p$ (Table).

Example 1

For determination of AN in White oil a sample of m=32.698 g was added to 50 mL of the reagent. After 3 min. stirring the mixture, $pH'_1=9.20$ was measured. The standard acid (0.1 mL of 0.03 M HCl) was added to the mixture and after 1 min of stirring $pH'_2=8.72$ was measured. Hence, AN=0.0026 mg KOH/g oil was calculated by eqn. 1. The average result and corresponding standard deviation for 5 oil samples ($AN_p$ and $S_p$) are given in the Table.

Example 2

A model of White oil fortified by naphthenic acid was prepared. A sample of the model of m=14.673 g was added to 50 mL of the reagent. After 3 min. of stirring the mixture of $pH'_1=8.99$ was measured. The standard acid (0.1 mL of 0.04 M HCl) was added into the mixture and after 1 min of stirring $pH'_2=8.60$ was measured. The value AN=0.0105 mg KOH/g oil was calculated by eqn. 1. The average result and corresponding standard deviation for 5 oil samples ($AN_p$ and $S_p$) are given in the Table.

Example 3

For determination of AN in Transformer oil (new) a sample of m=54.427 g was added to 50 mL of the reagent. After 3 min. stirring, $pH'_1=9.22$ was measured. Standard acid (0.1 mL of 0.04 M HCl) was added into the mixture and after 1 min of stirring $pH'_2=8.73$ was measured). The value AN=0.0020 mg KOH/g oil was calculated by eqn. 1. The average result and corresponding standard deviation for 5 oil samples ($AV_p$ and $S_p$) are given in the Table.

TABLE

Comparison of the results of AN determination by the standard titration technique and those obtained by the novel technique

| Ex. No. | Oil | Standard titration | | Proposed technique | | F | t |
|---|---|---|---|---|---|---|---|
| | | $AN_S$ | $S_S$ | $AN_P$ | $S_P$ | | |
| 1 | White | 0.0028 | 0.0001 | 0.0027 | 0.0001 | 1.31 | 2.07 |
| 2 | White fotrified | 0.0108 | 0.0004 | 0.0105 | 0.0003 | 0.47 | 0.96 |
| 3 | Transformer-New | 0.0020 | 0.0001 | 0.0019 | 0.0001 | 0.70 | 1.37 |
| 4 | Transformer-Used | 0.0043 | 0.0001 | 0.0042 | 0.0001 | 0.17 | 1.54 |
| 5 | Basic | 0.0060 | 0.0002 | 0.0061 | 0.0002 | 0.82 | 0.53 |

Example 4

For the determination of AN in used Transformer oil (used) a sample of m=29.356 g was added to 50 mL of the reagent. After 3 min. stirring $pH'_1=9.16$ was measured. The standard acid (0.1 mL of 0.04 M HCl) was added into the mixture and after 1 min of stirring $pH'_2=8.71$ was measured. The value AN=0.0042 mg KOH/g oil was calculated by eqn. 1. The average result and corresponding standard deviation for 5 oil samples ($AN_p$ and $S_p$) are given in the Table.

Example 5

For determination of AN in Basic oil a sample of m=10.665 g was added to 50 mL of the reagent. After 3 min. stirring $pH'_1=9.34$ was measured. The standard addition (0.05 mL of 0.04 m HCl) was introduced in the mixture and after 1 min of stirring $ph'_2=8.89$ was measured. The value AN=0.0058 mg KOH/g oil was calculated by eqn. 1. The average result and corresponding standard deviation for 5 oil samples ($AN_p$ and $S_p$) are given in the Table.

Precision and Accuracy of the Results

The average results obtained by standard titration and the novel technique from n=5 replicates for each $AN_s$ and $AN_p$, respectively; standard deviations for these replicates —$S_s$ and $S_p$, respectively; $F=S^2_p/S^2_s$ and $t=|AN_s-AN_p|/[(S^2_s+S^2_p)/5]^{0.5}$ are shown in the Table. The details of the experiments are described above (in "Examples").

The critical values for F-ratio is 6.39 at the 95% level of confidence and the number of degrees of freedom n−1=4. For t-ratio the critical value is 2.31 at the 95% level of confidence and the number of degrees of freedom 2(n−1)=8. From comparison of the F-data with the critical value it follows that differences between precision of results obtained by the standard titration and by the proposed technique are insignificant (all F are less than 6.39). The accuracy for these techniques is approximately the same so far as the deviations of the average AN results obtained by the novel technique from the average results obtained by the standard technique are insignificant in comparison with random errors (all t are less than 2.31).

The precision and accuracy obtained by the novel pH-metric technique are sufficient for quality control in industry.

Advantages of the Novel Reagent and it's Use

The reagent allows to determine low AN ($\times 3$-$10^{-2}$ mg KOH/g oil) by the pH-metric technique which is simple, rapid, low cost, using non-toxic solvents and suited to automation.

What is claimed is:

1. A reagent for a pH-metric acid number determination in a petroleum oil with low acid number, comprising:
   sodium benzoate; and,
   an alkali in a mixture of water and an alcohol.

2. The reagent according to according to claim 1, wherein the sodium benzoate is at a concentration of 0.02 to 0.1 mol/L.

3. The reagent according to claim 2, wherein the alcohol is isopropanol at a concentration of from 50% to 80% by volume.

4. The reagent according to claim 3, wherein the water is at a concentration of from 20% to 50% by volume.

5. The reagent according to claim 1, wherein the alcohol is isopropanol at a concentration of from 50% to 80% by volume.

6. The reagent according to claim 1, wherein the water is at a concentration of from 20% to 50% by volume.

7. The reagent according to claim 1, wherein the alkali is an hydroxide.

8. The reagent according to claim 7, wherein the hydroxide is potassium hydroxide.

9. The reagent according to according to claim 8, wherein the sodium benzoate is at a concentration of 0.02 to 0.1 mol/L.

10. The reagent according to claim 8, wherein the alcohol is isopropanol at a concentration of from 50% to 80% by volume.

11. The reagent according to claim 8, wherein the water is at a concentration of from 20% to 50% by volume.

12. The reagent according to claim 11, wherein the alcohol is isopropanol at a concentration of from 50% to 80% by volume.

13. The reagent according to claim 7, wherein the alcohol is isopropanol at a concentration of from 50% to 80% by volume.

14. The reagent according to claim 1, wherein the sodium benzoate and alkali are provided in a ratio that ensures a substantially complete extraction of acids from a petroleum oil to said reagent and a substantial completion of a reaction between benzoate anions and acids from the petroleum oil without significant influence of the hydrolysis of the benzoate anions, thereby allowing the pH-metric determination of the low acid numbers in the petroleum oil, with the low acid numbers being equal to, or less than, 0.03 mg KOH/g oil.

15. The reagent according to according to claim 14, wherein the sodium benzoate is at a concentration of 0.02 to 0.1 mol/L.

16. The reagent according to claim 14, wherein the alcohol is isopropanol at a concentratin of from 50% to 80% by volume.

17. The reagent according to claim 14, wherein the water is at a concentration of from 20% to 50% by volume.

18. A method for adjusting an alkali in a reagent for a pH-metric acid number determination in a petroleum oil with low acid numbers, said method comprising the steps of:
   providing a reagent comprising a salt of a strong base and a weak acid; and
   an alkali in a mixture of water and an alcohol,
   adjusting the alkali to provide a $pH'_o$, which is the pH of an equivalence-point on a titration curve of a strong acid added to a test portion of sodium benzoate, water and isopropanol.

19. The method according to claim 18, wherein the strong acid is hydrochloric acid.

20. The method according to claim 19, wherein said test portion has sodium benzoate in a concentration of from 0.02 to 0.1 M.

21. The method according to claim 20, wherein said test portion has isopropanol in a concentration of from 50% to 80% by volume.

22. The method according to claim 18, wherein said test portion has sodium benzoate in a concentration of from 0.02 to 0.1 M.

23. The method according to claim 18, wherein said test portion has isopropanol in a concentration of from 50% to 80% by volume.

24. The method according to claim 18, wherein the concentration of the alkali is adjusted to provide a conditional pH to the optimal pH'o value in the range of approximately 9.4 to approximately 10.4.

* * * * *